US010125418B2

(12) United States Patent
Gondal et al.

(10) Patent No.: US 10,125,418 B2
(45) Date of Patent: Nov. 13, 2018

(54) METHOD FOR THE PREPARATION OF AG/C NANOCOMPOSITE FILMS BY LASER-INDUCED CARBONIZATION OF ALKANE

(71) Applicant: KING FAHD UNIVERSITY OF PETROLEUM AND MINERALS, Dhahran (SA)

(72) Inventors: Mohammed Ashraf Gondal, Dhahran (SA); Radek Fajgar, Prague (CZ); Zain Hassan Abdallah Yamani, Dhahran (SA); Xiaofeng Chang, Nanjing (CN)

(73) Assignee: King Fahd University of Petroleum and Minerals, Dhahran (SA)

( * ) Notice: Subject to any disclaimer, the term of this patent is extended or adjusted under 35 U.S.C. 154(b) by 316 days.

(21) Appl. No.: 14/990,174

(22) Filed: Jan. 7, 2016

(65) Prior Publication Data
US 2016/0222502 A1 Aug. 4, 2016

Related U.S. Application Data

(60) Provisional application No. 62/110,189, filed on Jan. 30, 2015.

(51) Int. Cl.
C23C 14/28 (2006.01)
B01J 35/00 (2006.01)
(Continued)

(52) U.S. Cl.
CPC ............ *C23C 14/28* (2013.01); *A61L 31/084* (2013.01); *A61L 31/088* (2013.01); *A61L 31/16* (2013.01);
(Continued)

(58) Field of Classification Search
CPC ... C23C 14/28; C23C 14/223; C23C 14/0605; B01J 21/18; B01J 35/004; A61L 31/084; A61L 2420/06
See application file for complete search history.

(56) References Cited

U.S. PATENT DOCUMENTS

2002/0024297 A1* 2/2002 Kwok ................. H01L 51/0008
313/504
2009/0042751 A1* 2/2009 Narayan .............. C10M 141/00
508/155
(Continued)

OTHER PUBLICATIONS

M. Urbanová, D. Pokorná, S. Bakardjieva, J. Šubrt, Z. Bastl , P. Bezdi čka, J. Pola, IR laser-induced ablation of Ag in dielectric breakdown of gaseous hydrocarbons: Simultaneous occurrence of metastable hcp and stable fcc Ag nanostructures in C:H shell,Journal of Photochemistry and Photobiology A: Chemistry 213 (2010) 114-122.*

(Continued)

*Primary Examiner* — Bijan Ahvazi
(74) *Attorney, Agent, or Firm* — Oblon, McClelland, Maier & Neustadt, L.L.P.

(57) ABSTRACT

Ag/C crystalline nanocomposite films and a method of forming the films with controllable Ag/C molar ratios using a concurrent excimer laser-induced ablation of a silver target and a hydrocarbon gas under a vacuum atmosphere. Metal/Carbon nanocomposites prepared by concurrent irradiation of a metal target, in the presence of a hydrocarbon gas, during an excimer laser induced process.

14 Claims, 14 Drawing Sheets

(51) Int. Cl.
  *A61L 31/08* (2006.01)
  *B01J 21/18* (2006.01)
  *C23C 14/06* (2006.01)
  *C23C 14/22* (2006.01)
  *C23C 16/26* (2006.01)
  *C23C 16/44* (2006.01)
  *C23C 16/48* (2006.01)
  *A61L 31/16* (2006.01)
  *B32B 15/01* (2006.01)
  *C22C 5/06* (2006.01)
  *B22F 1/00* (2006.01)
  *B22F 1/02* (2006.01)
  *B22F 9/04* (2006.01)

(52) U.S. Cl.
  CPC ............ *B01J 21/18* (2013.01); *B01J 35/004* (2013.01); *B32B 15/01* (2013.01); *C22C 5/06* (2013.01); *C23C 14/06* (2013.01); *C23C 14/22* (2013.01); *C23C 16/26* (2013.01); *C23C 16/44* (2013.01); *C23C 16/4417* (2013.01); *C23C 16/483* (2013.01); *A61L 2300/104* (2013.01); *A61L 2400/12* (2013.01); *A61L 2420/04* (2013.01); *B22F 1/0018* (2013.01); *B22F 1/02* (2013.01); *B22F 9/04* (2013.01); *B22F 2201/30* (2013.01); *B22F 2202/11* (2013.01)

(56) References Cited

U.S. PATENT DOCUMENTS

2010/0307552 A1* 12/2010 Kohnke ............ H01L 31/02168
                                                        136/243
2012/0150275 A1*  6/2012 Shaw-Klein .............. A61F 2/88
                                                        623/1.15
2014/0342254 A1* 11/2014 Jennings ................. C01B 3/042
                                                        429/416

OTHER PUBLICATIONS

M. Janus, B. Tryba, M. Inagaki, A.W. Morawski, New preparation of a carbon-TiO2 photocatalyst by carbonization of n-hexane deposited on TiO2, Applied Catalysis B: Environmental 52 (2004) 61-67.*

Mohammed Ashraf Gondal, et al., "ArF excimer laser-induced deposition of Ag/C nanocomposite thin films in the presence of n-Hexane", Applied Surface Science, vol. 311, 2014, pp. 95-100.

M. Urbanova, et al., "IR laser-induced ablation of Ag in dielectric breakdown of gaseous hydrocarbons: Simultaneous occurrence of metastable hcp and stable fcc Ag nanostructures in C:H shell", Journal of Photochemistry and Photobiology A: Chemistry, vol. 213, Issues 2-3, Jun. 25, 2010, pp. 114-122 (Abstract only).

Vincenzo Amendola, et al., "Laser Ablation Synthesis of Silver Nanoparticles Embedded in Graphitic Carbon Matrix", Science of Advanced Materials, vol. 4, No. 3/4, 2012, pp. 1-4.

Dana Pokorná, et al., "Laser ablation of Ga in dielectric breakdown of gaseous hydrocarbons: deposition of ambient-pressure unstable Ga nanophases in carbonaceous environment", Journal of Photochemistry and Photobiology A: Chemistry, vol. 215, Issues 2-3, Sep. 25, 2010, pp. 164-171 (Abstract only).

M. Janus, et al., "New preparation of a carbon-$TiO_2$ photocatalyst by carbonization of n-hexane deposited on $TiO_2$", Applied Catalysis B: Environmental, vol. 52, Issue 1, Sep. 8, 2004, pp. 61-67 (Abstract only).

* cited by examiner

METHOD FOR THE PREPARATION OF AG/C NANOCOMPOSITE FILMS BY LASER-INDUCED CARBONIZATION OF ALKANE

CROSS-REFERENCE TO PROVISIONAL APPLICATION

This application claims priority to U.S. Provisional Application No. 62/110,189, filed Jan. 30, 2015; the disclosure of which is incorporated herein by reference in its entirety.

BACKGROUND OF THE INVENTION

Technical Field

The present disclosure is directed to a method of preparing a metal/carbon nanocomposite and nanocomposite thin films made by the method, the use of the nanocomposite films as plasmonic photocatalysts, in SERS-based sensors, as biomedical coatings, and for antimicrobial applications such as water remediation. More specifically, the disclosure is directed to an excimer laser irradiation process for the preparation of textured Ag/C nanocomposite thin films.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Nanomaterials, such as nanocomposites, are multiphase solid materials wherein one of the phases has one, two or three dimensions of less than 100 nanometers (nm), or structures having nano-scale repeat distances between the different phases that make up the material. The properties of nanocomposites are determined not only by the morphology and spatial distribution of the nanophase, but also depend on mutual chemical and physical interactions between the various phases involved. Furthermore, a nanocomposite is any composite material, one or more, of whose components are some form of nanoparticle. Nanoparticles, by definition, are particles between 1 nm and 100 nm in size. In nanotechnology, a particle is defined as a small object that behaves as a whole unit with respect to its transport and properties.

Metal nanoparticles, in particular, are recognized as being important contributors to the fields of chemistry, physics and biology due to their unique optical, electrical and photothermal properties. Such metallic nanoparticles have great potential for application in laboratory settings, as they can be used as probes in mass spectroscopy, and can also be employed in the colorimetric detection of proteins and DNA molecules. Metal nanoparticles have furthermore been used for therapeutic applications and drug delivery. One metal of great interest is silver, in both nanoparticle and nanocomposite form.

Silver nanoparticle-based materials have recently gained great interest due to their potential for use in a variety of fields, such as selective heterogeneous catalysis. Heterogeneous catalysis, in chemistry, refers to the form of catalysis where the phase of the catalyst differs from that of the reactants. This can include catalysis reactions such as hydrogenation, [B. J. Li, H. B. Li, Z. Xu, Experimental evidence for the interface interaction in Ag/C60 nanocomposite catalyst and its crucial influence on catalytic performance. J. Phys. Chem. C 11 (2009) 21526-21530 Incorporated by reference herein in its entirety], oxidation, [S. Y. Wu, Y. S. Ding, X. M. Zhang, H. O. Tang, L. Chen, B. X. Li. Structure and morphology controllable synthesis of Ag/carbon hybrid with ionic liquid as soft-template and their catalytic properties. J. Solid State Chem. 2008, 181 (2008) 2171-2177. Incorporated by reference herein in its entirety], and hydrogen storage [S. Rather, M. Naik, S. W. Hwang, A. R. Kim, K. S. Nahm. Room temperature hydrogen uptake of carbon nanotubes promoted by silver metal catalyst. J. Alloy Compd. 475 (2009) L17-L21 Incorporated herein by reference in its entirety].

Additionally, for many applications, the use of spherical nanoparticles is desired. Methods are needed for consistent production of spherical metal nanoparticles for incorporation into nanocomposites. Moreover, there is also need for the development of cubic nanoparticles as well. Cubic nanoparticles, such as those incorporated into gold and silver nanocomposites, can be used to amplify the difference in left- and right-handed molecules' response to circularly polarized light. Several studies have indicate that these cubic nanoparticles provide the basis for probing the effects of chirality, or handedness, in molecular interactions with increased sensitivity over prior methods [Fang Lu, Ye Tian, Mingzhao Liu, Dong Su, Hui Zhang, Alexander O. Govorov, Oleg Gang, Discrete Nanocubes as Plasmonic Reporters of Molecular Chirality Nano Lett., 2013, 13 (7), pp 3145-3151DOI: 10.1021/nl401107 g Publication Date (Web): Jun. 18, 2013 American Chemical Society, Incorporated herein by reference in its entirety]. There is a need for rapid methods of synthesizing both spherical and cubic silver nanoparticles, given their wide range of applications.

In addition to gold/silver nanocomposites, silver nanoparticle-based materials can incorporate other components, such as carbon, to form a nanocomposite indicated by Ag/C which signifies a core/shell structure, in which Ag is the core and C forms the shell. Herein "/" indicates a core/shell form. In such form, Silver/Carbon nanocomposites have a wide array of applications, including catalysis.

Metal nanoparticles have proven effective as plasmonic photocatalysts due to their surface plasmon resonance effects. Surface plasmon resonance (SPR) relates to the enhanced reflectivity of a dielectric material. Recently, due to the SPR effect of silver nanoparticles, silver/carbon nanocomposites were reported as efficient plasmonic photocatalysts due to their enhanced reflectivity under visible light [S. M. Sun, W. Z. Wang, L. Zhang, M. Shang, L. Wang. Ag/C core/shell nanocomposite as a highly efficient plasmonic photocatalyst. Catal. Commun. 11 (2009) 290-293. Incorporated herein by reference in its entirety]. Additionally, Ag/C nanocomposites have exhibited high photocatalytic activity in the decomposition of aqueous and gaseous compounds under visible-light irradiation. The origin of this high photocatalytic activity is mainly ascribed to the surface plasmon resonance (SPR) effect of silver nanoparticles in the Ag/C composite. Thus, these Ag/C nanocomposites are considered to be promising materials for use in solar light harvesting devices and sensors due to their photocatalytic activity.

In addition to the above applications, Ag/C nanostructures are important for biological applications due to the surface functional groups provided by the carbonaceous products [S. Li, X. Yan, Z. Yang, Y. Yang, X. Liu, J. Zou. Preparation and antibacterial property of silver decorated carbon microspheres. Appl. Surf. Sci. 292 (2014) 480-487. Y. Zhao, Z. Q. Wang, X. Zhao, W. Li, S. X. Liu. Antibacterial action of silver-doped activated carbon prepared by vacuum impregnation. Appl. Surf. Sci. 266 (2013) 67-72. X. M. Sun, Y. D. Li. Ag/C core/shell structured nanoparticles: controlled synthesis, characterization, and assembly. Langmuir 21 (2005) 6019-6024. Incorporated herein by reference in their entirety]. The antibacterial role of the Ag/C nanocomposites is due to the toxicity of silver to microbes, and the use of silver nanoparticles is of interest because of the slower, more controlled release of silver ions. The slower release of silver cations, from silver nanoparticles and/or silver/carbon nanocomposites, can avoid the constant delivery of an excess amount of silver to the area compared with other $Ag^+$ based chemicals. Also, in using silver nanoparticles and nanocomposites, the metallic silver is not as susceptible to deactivation by a chloride molecule as compared with silver ions [Dunn, K.; Edwards-Jones, V. *The role of Acticoat with nanocrystalline silver in the management of burns*; Wythenshawe Hospital Burns Unit, Manchester, UK: England: United Kingdom, 2004; pp S1-9, Incorporated herein by reference in its entirety.]

There is a considerable interest and need for the advancement of preparation techniques for metal nanoparticle, metal/carbon nanocomposites, and specifically, Ag/C nanocomposites, also described as core/shell nanocomposites. The preparation of metal/carbon nanocomposite thin films, such as Ag/C nanocomposite thin films, wherein texture variations result from differences in the molar ratio of carbon to the metal nanoparticle core is of further interest.

The preparation of silver and carbon core/shell composites has been reported by both chemical and photochemical methods [S. M. Sun, W. Z. Wang, L. Zhang, M. Shang, L. Wang. Ag/C core/shell nanocomposite as a highly efficient plasmonic photocatalyst. Catal. Commun. 11 (2009) 290-293., X. M. Sun, Y. D. Li. Ag/C core/shell structured nanoparticles: controlled synthesis, characterization, and assembly. Langmuir 21 (2005) 6019-6024, Incorporated herein by reference in their entirety.] However, these processes have disadvantages, in that they require significantly lengthy production times for synthesis, and the resulting silver particle size distribution is not narrow. Furthermore, prior methods for forming silver carbon nanoparticles utilize surfactants and suffer from issues with agglomeration, low volume production, and impurity.

The use of metal/carbon nanocomposites in the formation of thin films is an additional area of research for which there is considerable interest and need for advancement. Nanocomposite thin films possess improved mechanical, electronic and magnetic properties as a result of several factors, such as crystallite size and textures. These factors depend significantly on the material selection, deposition methods, and process parameters in forming the nanocomposite thin films. Materials for nanocomposite thin films include, but are not limited to metals, such as silver, gold, palladium, nickel, cobalt, and non-metals such as carbon and nitrogen. By definition, thin film composites can include particles, both microparticles and nanoparticles, dispersed therein. Nanocomposite films comprise at least two phases, a nanocrystalline phase and an amorphous phase, or alternatively, a nanocrystalline phase with another nanocrystalline phase [S. Zhang, Y. Fu, H. Du, Y. Liu, T. Chen, Nanocomposite Thin Films for both Mechanical and Functional Applications 2004 dspace.MIT-edu. Incorporated herein by reference in its entirety.] Due to their unique physical-chemical properties, nanocomposite thin films have recently gained interest for use in both the mechanical and functional fields, and furthermore, metal/carbon nanocomposites and nanocomposite thin films have been described as lubricants for solid surfaces.

Techniques for preparation of nanocomposite films include, but are not limited to, magnetron sputtering, chemical vapor deposition, and laser ablation. In considering laser ablation methods, there are many types of lasers that can be employed; each operating at a defined wavelength of light. In view of optical properties, excimer lasers possess advantages over other types of lasers, including the Nd:YAG laser, in thin film manufacturing. The advantages are largely based on their superior ablation characteristics and much better energy stability. Major drawbacks of the Nd:YAG lasers for pulsed laser deposition (PLD) include a Gaussian beam profile instead of a flat-top profile, as well as temperature-induced polarization and thermal lensing effects which can create donut-shaped beam profiles and lateral distortions. [Pulsed laser deposition—UV laser sources and applications R. Delmdahl, R. Pätzel Coherent GmbH, Hans-Böckler-Str. 12, D-37079 Göttingen, Germany PACS 42.55.Lt, 52.38.Mf, 81.15.Gh Incorporated herein by reference in its entirety.]

New preparation methods are sought to overcome disadvantages with the conventional preparation of metal/carbon nanoparticles and metal/carbon nanocomposite thin films. Accordingly, one objective of the present disclosure is to provide methods or processes of preparing nanocomposites and nanocomposite thin films.

BRIEF SUMMARY OF THE INVENTION

The present disclosure relates to a method and apparatus for the preparation of uniformly sized and stable nanoparticles and nanocomposites, and their use to form nanocomposite thin films.

According to a first embodiment, the present invention is directed to a method of preparing a core/shell nanocomposite thin film comprising:

concurrently irradiating a metal target and a hydrocarbon gas, present within a deposition chamber, with an excimer laser beam;

wherein the irradiating forms carbon for example in the form of graphite from the hydrocarbon gas, and nanoparticles of said metal target, and concurrently forms core/shell nanocomposite particles having a metal core covered by a carbon shell;

wherein the core/shell nanocomposite particles form a nanocomposite thin film on a substrate within the deposition chamber;

wherein the pressure of the hydrocarbon gas in the deposition chamber during the irradiating is within a range of 20-100 Pascals.

In a further embodiment, the nanocomposite thin film of a thickness in the range of 200 nm to 1000 nm and texture in the range of 1 nm to 10 nm is formed within the time range of 30-90 seconds of the irradiating.

In a further embodiment, the hydrocarbon is selected from the group consisting of a $C_1$-$C_{10}$ alkane and a $C_1$-$C_{10}$ alkene.

In a preferred embodiment, the $C_1$-$C_{10}$ alkane is n-hexane.

In a further embodiment, the method further comprises varying the pressure of the hydrocarbon gas to result in a variation of a mass ratio of carbon to metal in the core/shell nanocomposite particles.

In a further embodiment, the irradiating forms core/shell nanocomposite particles having an average particle size of 5-20 nm in diameter.

In a further embodiment, the nanoparticles are either spherical or cubic in form.

In a further embodiment, the metal is a transitional metal selected from the group consisting of Group 9, 10, or 11 transitional metals.

In a preferred embodiment, the transitional metal is silver.

In a further embodiment, the excimer laser beam is generated by an excimer laser selected from the group consisting of ArF and KrF excimer lasers having a beam wavelength of 193 nm-248 nm.

In a preferred embodiment, the excimer laser is the ArF excimer laser with a wavelength of 193 nm.

In a further embodiment, the core/shell nanocomposites formed by the irradiating have absorption peaks in a range from 417 nm-525 nm and further comprise a core of silver (Ag) and a shell of carbon (C).

In a further embodiment the disclosure relates to a thin film of nanoparticles formed by the method of our first embodiment having a thickness of 200 to 1000 nm.

In a further embodiment the disclosure relates to a thin film of nanoparticles formed by the method of our first embodiment wherein the ratio of carbon to silver varies from 1.10:1.00 to 1.75:1.00.

In a further embodiment the disclosure relates to a thin film of nanoparticles formed by the method of our first embodiment wherein increasing the pressure of the hydrocarbon gas from 20 Pa to 100 Pa results in a much thinner film.

In a further embodiment, a textured nanocomposite thin film is used in solar light harvesting devices.

In a further embodiment, a textured nanocomposite thin film is used in water purification applications.

In a preferred embodiment, the water purification application is plasmonic photocatalysis.

In a further preferred embodiment, the water purification application is a nanocomposite thin film surface-enhanced Raman spectroscopy ("SERS")—based sensor for the detection of contaminants in an aqueous phase.

In a further embodiment, a textured nanocomposite thin film is used as a coating for biomedical devices.

In a further preferred embodiment, the biomedical device is a stent.

According to a second embodiment, the present disclosure relates to a method for forming a silver/carbon nanocomposite from a solid silver target during an excimer laser ablation process comprising:

providing a deposition chamber;

placing a silver metal target and a substrate within said deposition chamber;

establishing a vacuum level within said deposition chamber so as to achieve a reduced atmospheric pressure;

introducing a hydrocarbon into said deposition chamber wherein said hydrocarbon is in a vapor phase due to the reduced atmospheric pressure and furthermore wherein said hydrocarbon vapor fills said deposition chamber and is in contact with said silver target;

focusing an excimer laser beam onto the silver target in contact with the gaseous hydrocarbon at a power density high enough to release cubic or spherical uniformly-sized nanoparticles of the silver from the silver substrate;

concurrently irradiating said hydrocarbon gas with the excimer laser beam at a power density high enough to cause decomposition of the hydrocarbon gas;

said irradiation causing a carbonization of said silver nanoparticles to form a silver/carbon nanocomposite collecting said silver/carbon nanocomposite on said substrate to form a nanocomposite thin film;

wherein varying the chamber vacuum level results in fluctuation of the hydrocarbon vapor pressure in the range of 20-100 Pascals, affecting the ratio of carbon to silver in the silver/carbon nanocomposite, and furthermore resulting in deposition texture variations of the nanocomposite thin film.

Therefore, the present disclosure relates to the preparation of a series of Ag/C nanocomposite textures with a controllable mass ratio of silver to carbon, via an excimer laser induced process, in the presence of n-hexane as the carbonaceous precursor.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
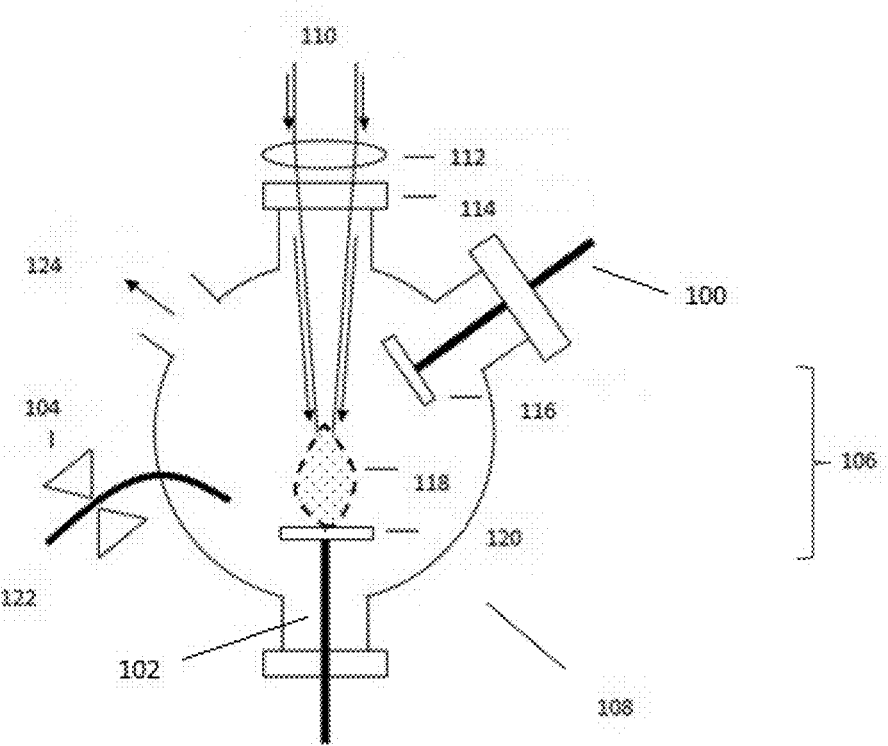
FIG. 1 shows a schematic diagram of experimental setups for deposition of Ag/C nanocomposite textures.

Referring now to the drawings, wherein like reference numerals designate identical or corresponding parts throughout the several views.

The present disclosure pertains to a method for preparing silver/carbon nanocomposites. Herein the present disclosure combines the advantages of performing laser ablation of a metal target in a dry atmosphere, with the simultaneous decomposition of a hydrocarbon, triggered by the controlled interaction of the laser energy, material and ambient hydrocarbon gas, thus forming a carbonized metal nanocomposite, and further a carbonized metal nanocomposite thin film.

One primary use for silver/carbon nanocomposites and composite films is water remediation. Previously, suitable anchoring substrates were not available; therefore much of the silver nanoparticle or nanocomposite catalyst was lost to its undesirable release into the water. Therefore, prior water remediation has been hampered by the great difficulty of using catalysts in their powdered form for heterogeneous plasmonic photocatalysis applications. Thin film preparation of a metal/carbon nanocomposite on a suitable anchoring substrate will result in the simplification of the recycling process from an aqueous solution. Thin film preparation techniques, resulting in the rapid production of stable metal/carbon nanocomposites for use in water remediation, is therefore necessitated. Further water purification applications include the antibacterial properties of the silver ion, and the use of the Ag/C nanocomposites as possessing antibacterial properties.

The Ag/C nanocomposites and nanocomposite thin films can be included in SERS based sensors for the detection of contaminants in an aqueous phase, such as water. As such, purification systems and water purification applications are greatly improved.

The Ag/C nanocomposites and nanocomposite thin films of the present disclosure have a role in biomedical devices. Medical devices or implants that are in contact with body fluids or body tissues, such as catheters, electrodes, and implants, are susceptible to immune reactions, formation of a thrombus, inflammation, and infection. In order to avoid these conditions, the surfaces of the biomedical devices can be coated with the Ag/C nanocomposites and nanocomposite thin films, for example in a form immobilized on a surface, or covalently bonded with biocompatible molecules. One application of the silver/carbon nanocomposite thin film is for use on tubular intravascular stents, which may comprise a radially expandable mesh type metal network. This metal network tends to be thrombogenic. It is within the scope of this disclosure to utilize specific coating parameters and fixturing techniques in order to coat stents, and other medical devices and implants, with a flexible and fully encapsulating Ag/C nanocomposite film. The advantage of this biocompatible Ag/C thin film is increased flexibility over traditional diamond like carbon films and the inclusion of silver for antimicrobial/antibacterial effects. More specifically, by controlling the deposition pressures during formation of the nanocomposite thin films, it is possible to produce biocompatible nanocomposite thin films for use on stents or other related bio-medical applications with varying amounts of carbon to silver molar ratios.

Ag/C crystalline nanocomposite textures with controllable Ag/C molar ratios have been developed using an excimer laser-induced ablation process and silver target under an alkane atmosphere, e.g., n-hexane atmosphere.

Laser ablation has advantages in fabricating nanocomposites because a large amount of atom clusters, or nanoparticles, are formed during the ablation process. The shape of the nanoparticles ablated from the target surface material is also a significant and necessary characteristic in defining how a nanoparticle acts, interacts, or can be acted upon. Spherical and cubic particles are desirable for their uniform shape and repeatable characteristics. Laser processing can form very high-quality nanoscale particles of generally spheroid morphology and exceptionally tight particle size distribution. Additionally, these laser-induced ablations are very fast in comparison to magnetron sputtering and chemical vapor deposition methods.

In view of optical properties, the excimer laser, also known as an exciplex laser, possesses advantages over other types of lasers, including the Nd:YAG laser, in thin film manufacturing. These advantages include superior ablation characteristics and much better energy stability. An excimer laser is a form of ultraviolet laser which emits a cool beam of ultraviolet light. The excimer laser typically uses a mixture of a noble gas (argon, krypton, or xenon), and a halogen gas such as fluorine or chlorine. When the laser pulse is absorbed by a surface material target, energy is first converted to electronic excitation and then into thermal, chemical and mechanical energy resulting in evaporation, ablation, plasma formation and even exfoliation. In a preferred embodiment, during application, an excimer laser adds enough energy to disrupt the molecular bonds of the surface of the target material, resulting in the ejection of matter from the surface of a solid metal target material in a tightly controlled manner through ablation. At sufficiently high laser powers, the ejected material can be further excited to a plasma phase or plume, or an ejecta event in a vacuum phase. In the present disclosure, the use of the term plume or ejecta event will signify the ablation of the target metal into a stream comprising nanoparticles. Concurrently, the decomposition of the hydrocarbon into carbon and/or graphite takes place under excimer laser beam irradiation. A laser ablative pulse gives rise to the decomposition of the hydrocarbon gas into smaller molecules and ions, by thermal or photo-chemical decomposition. Excimer lasers have the useful property that they can remove exceptionally fine layers of surface material with almost no heating or change to the remainder of the material which is left intact, while concurrently interacting with a gaseous environment to decompose said gaseous components into their atomic constituents. Furthermore, excimer lasers provide the shortest commercially available wavelengths and correspondingly, the highest commercially available photon energies for laser material processing. Depending on the laser gas, the emission of excimer lasers covers a range of wavelengths from 157 nm to 351 nm. In conjunction with its high ultraviolet output energies, an excimer laser ablation process offers great flexibility in terms of the target material spectrum and the ablation area. Furthermore, the high energy photons of the excimer laser allow virtually all target materials to be deposited, including such materials as oxides, nitrides, and carbides. Process stability and thin film quality in Pulsed Laser Deposition (PLD) procedures largely benefit from the exceptional pulse-to-pulse stability of the excimer laser radiation. The top-hat beam profile, which is imaged on the sample, minimizes fractionation during the ablation process and supports stoichiometric transfer from the target material to a substrate, thus enabling a controlled thin film deposition.

In a preferred embodiment, an argon fluoride laser (ArF laser) is used to carry out the method of this disclosure. It is a deep ultraviolet excimer laser, having an emission wavelength of 193 nm, and may be used in the production of semiconductor integrated circuits, eye surgery, micromachining, and scientific research. Other excimer lasers, such as the KrF laser, with a wavelength of 248 nm, may also be capable of producing the metal/carbon nanocomposite textures as well.

Pulsed laser deposition occurs when a high-power pulsed laser beam is focused inside a vacuum chamber to strike a target of material which deposits to form a film. This material is vaporized from the target, which deposits as a thin film on a substrate. More specifically, the ejected species expand into the surrounding vacuum in the form of an ejecta plume or ejecta spray containing many energetic species including atoms, molecules, electrons, ions, clusters, before depositing on a substrate. This process typically occurs under reduced pressure, 100-900 mTorr, for example, preferably 200-800 mTorr, or 300-500 mTorr. It may also take place in the presence of a background, or 'assist' gas, which can be used to provide a second target material, and reaction of the two target materials thus forming a nanocomposite. The byproducts of the laser induced hydrocarbon decomposition process when combined with the ablated metal species can form metal/carbon nanocomposites.

A solid target, which may be in the form of microparticles, is employed as the starting material in the production of nanoparticles, and nanocomposites. Microparticles can be composed of a wide variety of materials of any shape. Preferably, such materials are solid at room temperature and are not susceptible to chemical degradation during the practice of the present disclosure. Representative examples of suitable materials include Group 9, 10, and 11 transitional Metals such as gold, silver, palladium, platinum, nickel, iron and cobalt.

The first step in the creation of uniformly sized and cubic or spherical shaped nanoparticles is ablation of a target surface to create a plume or ejecta event which moves radially away from the surface of the target material. In a heavy atmosphere, i.e. a fluid medium, this ejecta event is known as an ejecta plume which has a Knudsen boundary layer separating the vapor within the plume (which contains the ejecta material) from the heavy atmosphere. In a vacuum, vaporization and/or ablation of metal particles is preferably accomplished by delivering a specific energy packet (typically photon or electric energy) to the target surface. This becomes phonon energy within the target surface which is sufficient to break the intra-nuclear bonds around small clusters of atoms, and further eject clusters away from the target surface at a rate which reduces residual heat within the target material that may lead to ion production. Altering the physical properties of the target material affects the ablation rate of that target. For instance, annealed metal targets, such as Ag, have reduced intra-nuclear bonding energies and thus produce particles at higher rates from a constant energy delivered.

Assist gasses can be used to modify the environment in which the laser process occurs. If a hydrocarbon gas is supplied to the laser interaction zone, a decomposition reaction, ignited by the laser pulse, will result in the generation of carbon and carbonaceous products with partial or complete graphite-like structures. The excimer laser strikes the hydrocarbon vapor to decompose it and initiate particle nucleation in a reaction zone. Low molecular carbonaceous species can be produced by simultaneous dielectric breakdown of a hydrocarbon gas by the excimer laser beam. Under certain conditions it may be possible to cause the generation of a liquid hydrocarbon phase at the surface of the metal target.

The hydrocarbon gases of this disclosure may be in a liquid form prior to vacuum treatment to render them into their gaseous phase. Additionally the hydrocarbon, when initially in a liquid phase, may undergo distillation to remove impurities prior to placing it on a vacuum line. It is within the scope of the present disclosure to use hydrocarbons such as methane, ethane and/or ethylene in this process. Representative examples of a suitable hydrocarbon include linear or branched hydrocarbons, along with cyclic or aromatic hydrocarbons. In a preferred embodiment, the hydrocarbon is selected from the group consisting of short- medium- and long chained inert carbonaceous gases. In a further preferred embodiment, the hydrocarbon is a straight-chained alkane or an alkene. In a most preferred embodiment, the hydrocarbon is selected from the group consisting of, but not limited to, $C_3$-$C_{10}$ n-alkane or n-alkene hydrocarbons, which include n-propane, n-butane, n-pentane, n-hexane, n-heptane, n-octane, n-nonane, and n-decane, as well as n-propene, n-butene, n-pentene, n-hexene, n-heptene, n-octene, n-nonene and n-decene, and branched derivatives thereof. It is also within the scope of this invention to deliver more than one alkane or alkene, or combination thereof, hydrocarbon gas into the deposition chamber. In a most preferred embodiment, the hydrocarbon is n-hexane. The approach in this invention is to deliver a hydrocarbon gas, or gases, into the deposition chamber, where a suitable combination of the excimer laser, the metal material being irradiated, and thus ablated, the feature being formed by ablation, and pressure within the deposition chamber can be selected so as to form a nanocomposite thin film of selected texture in the laser ablation process.

It is desirable to confine the hydrocarbon gas and the solid metal substrate target material so that they interact. This can be achieved by selecting a structure which suitably contains the hydrocarbon vapor and the solid metal substrate target so that the excimer laser can interact with both, and so that upon ablation, interaction of the hydrocarbon gas, or decomposition products thereof, and the ablated plume of metal nanoparticles can ensue. Such confinement can occur in a deposition chamber such as a reactor as shown in FIG. 1, which may be spherical in form and may be made of amorphous glass. It is desirable that an appropriate mass flow rate of the hydrocarbon is maintained so that said hydrocarbon remains in gas phase, that, when exposed to the excimer laser beam, results in the formation of carbon atoms for carbonization of the metal nanoparticles released by the solid metal target material during ablation with the excimer laser beam.

In a preferred embodiment, the pressure of the n-alkane (n-hexane) may be adjusted such that the laser beam has interaction with the hydrocarbon gas at an optimal pressure within the range of 20-100 Pascals. The molar ratio of carbon to silver can be controlled through adjusting the n-alkane (n-hexane) pressure, producing spherical or cubic silver nanoparticles with a size range of 5-20 nm and a relatively narrow size distribution, thus providing a means of controlling the thickness and texture of the nanocomposite thin-film.

Reference is now made to FIG. 1 showing a representative laser deposition system 106 for performing the method of the present invention. As shown, the experimental pulsed laser deposition system 106 includes a vacuum deposition chamber 108 and a laser system (not shown). The vacuum deposition chamber is designed to confine all of the reactants of the laser ablation process. In a preferred embodiment, the deposition chamber 108 is a spherical glass reactor having a diameter in the range of 10-15 cm. The deposition chamber may contain several windows 114 for viewing and for the transmission of laser energy, only one of which is shown for clarity. A vacuum pump 124 is provided to evacuate the deposition chamber during the pulsed laser deposition process. As will be described in greater detail below, a pulsed laser beam 110 is used to irradiate a target within the vacuum deposition chamber 108 in order to deposit ablated material(s) on a substrate 116. Further, one skilled in the art will recognize and understand that all material surfaces within the chamber, input and output ports, tubing and static fixture materials are preferentially nonreactive, non-attractive and non-absorbent to or with the specific nanoparticles being created. For example, untreated glass and quartz will readily absorb many types of nanoparticles, particularly metallic particles and pose substantial problems for use as materials for the reaction chamber. Preferred materials for carrying out the preferred method of this invention include Teflon, PTFE, PEEK, and PET.

A primary excimer laser emits or delivers a discrete energy packet of photon energy in a pulsed manner. Laser beam 110 is generated by an excimer laser (not shown). Any commercially available excimer laser capable of generating a laser light in the ultra violet wavelengths in the range from 157 nm to 351 nm can be employed. In one embodiment, irradiation conditions range from 1 s-120 s in time, with a repetitive frequency of 5 to 15 Hz, and an energy range of 50 mJ/pulse to 100 mJ/pulse. In a preferred embodiment, irradiation conditions range from 55 s-65 s in time, with a repetitive frequency of 9 to 11 Hz, and an energy range of 70 mJ/pulse to 90 mJ/pulse. In a most preferred embodiment, irradiation occurs for a 60 s time interval, with a repetitive frequency of 10 Hz, and an energy of 80 mJ/pulse.

The selection of a specific laser depends on the optical properties of the microparticles and the size of the nanoparticles desired. In a preferred embodiment, laser beam 110 with a wavelength range of 193-300 nm, can be generated using an ArF excimer laser. In a most preferred embodiment, laser beam 110 with a wavelength of 193 nm is generated using an ArF excimer laser. Additionally, laser beam 110 can be generated with a KrF excimer laser having a wavelength of 248 nm.

In order to carry out the method of the present invention, a target 120 and a substrate 116 were placed within the deposition chamber 108. The target 120 material can be any of a number of Group 9, 10, or 11 transition metals such as silver, gold, platinum, nickel, cobalt or palladium. In a preferred embodiment, the target material is silver. The substrate 116 upon which the nanocomposite will be deposited is a non-reactive substance. Untreated quartz, amorphous glass and polished NaCl will all readily absorb many types of nanoparticles, particularly metallic nanoparticles and can be used as a surface substrate 116 for the formation of the Ag/C nanoparticles, or other metal/carbon nanoparticles, and resulting films. In a preferred embodiment the substrate is amorphous glass. In an alternate preferred embodiment, the substrate is polished NaCl. Furthermore, the sample collector 116 is positioned at an opposite side of the hydrocarbon gas inlet tube so that the sample collector is placed in the path of the laser-irradiated and therefore, laser-ablated material.

According to an important aspect of the present invention, the deposition chamber 108 is evacuated to a relatively moderate vacuum level, in the range of 20 to 100 Pascals. The hydrocarbon gas enters the deposition chamber 108 via a gas inlet line 122. Flow controller 104 is a polytetrafluoroethylene (PTFE) stopcock valve used to restrict or isolate the flow of the gas thru the line of the aerosol feed source 122 from a pressurized gas source (not shown). The hydrocarbon gas is introduced into the deposition chamber 108 in a manner so that it reacts with the plasma ejecta plume 118 created when the target is irradiated, forming a nanocomposite material which is directed toward the substrate 116 for deposition of the material thereon. The hydrocarbon gas flow is introduced and delivered in the direction of the line through a line 122 so that it purges other ambient gases from the deposition chamber prior to irradiating with the laser. As previously stated, line 122 is connected to a source of hydrocarbon liquid (not shown) which is distilled on a vacuum line and furthermore rendered into its gas phase under reduced pressure prior to entering line 122. In a further preferred embodiment, the alkane hydrocarbon is n-hexane. The hydrocarbon gas fills chamber so as to fill voids remaining after the target 120, substrate 116, and static supporting fixtures 100 and 102 are placed within the deposition chamber. The hydrocarbon gas is found under these conditions within the deposition chamber 108 before any laser reaction is initiated and takes place. The pressure is monitored and controlled by a pressure sensor (not shown) and an equipped stopcock valve 104. In a preferred embodiment the pressure sensor is an Edward Barocel. In a preferred embodiment the stopcock valve 104 is made of a non-reactive material such that it does not collect any nanoparticulate, graphite or nanocomposites.

Laser beam 110 is introduced into the vacuum deposition chamber 108 at an angle of 180° which may vary by +/−5° after passing through a spherical converging lens 112 (f=30), the focal length being the distance at which a beam of collimated light will be focused to a single spot, and enters through a quartz glass window 114 before converging on the target metal 120. Furthermore the beam 110 is focused on the surface of the metal target material 120 which is placed on a static fixture 102 inside the deposition chamber 108. As the excimer laser (not shown) emits or delivers a discrete energy packet of photon energy via the laser beam 110, laser irradiation and furthermore, ablation, takes place. Once a pulse from emission 110 interacts with the surface of the target 120, the energy of the laser photons transfers into the lattice structure of the target 120 becoming a phonon. This energy breaks the intra-nuclear bonds within the lattice structure and releases particles from the target 120 surface. This creates ablated particles within an ejecta plume.

The utilization of a hydrocarbon atmosphere, as the laser emission 110 interacts with the target 120, the ablated particles form an initial ejecta plume containing discrete plume 118 to be deflected towards a substrate on which the nanoparticles and or nanocomposites can form. During the process, nanoparticles are collected or deposited on a substrate 116, said substrate held in place by a static fixture 100.

In order to facilitate continuous production and removal of the ablated and carbonized particles, the chamber contains a gas inlet line 122 and evacuation output port 112 which are connected through input and output tubing or piping or other similar structures to a tank or other similar holding vessels or chambers that contains the desired fluid, whether liquid or gas or other heavy atmosphere. A mechanism for mixing the desired fluid, whether by stirring or other mechanism may be included. The pressure in gas systems can be controlled by controlling the gas pressure. Similarly, in vacuum systems, the creation and maintenance of the vacuum within the system will operate with commonly understood components. The tank can further include a sample port (not shown) which could also include sensors for temperature, and/or fluid volume.

In a preferred embodiment, n-hexane underwent distillation on a vacuum line (not shown) prior to entering the deposition chamber 108 via the gas line 122. Flow was adjusted by flow controller PTFE stopcock 104 so that n-hexane pressure was in the range of 20-100 Pascals, or the equivalent range of 150-750 mTorr. The pressure was monitored and controlled by an Edwards Barocel pressure sensor (not shown) and equipped with PTFE flow controller valve 104. According to an important aspect of the invention, n-hexane underwent decomposition and dielectric breakdown via an excimer laser to yield low molecular carbonaceous species. The carbonization process takes place adjacent to the silver microparticle mass. The simultaneous dielectric breakdown, or decomposition, of n-hexane and the ablation of silver by the excimer laser results in the formation of a low molecular weight carbonaceous species, along with spherical or cubic silver nanoparticles of a relatively small size distribution of 5-20 nm. The presence of the carbonaceous species, preferably in a graphite form, allows the formation of a covering, or shell encompassing the silver nanoparticles, resulting in Ag/C nanocomposites which are crystalline in structure. The Ag/C molar ratios can be controlled via the variation of the pressure of the alkane. In particular the pressure of n-hexane adjusted within the range of 20-100 Pa, more specifically within a sub-range of 20-80 Pa, most specifically within the range of 50-70 Pa, influences the molar ratio of carbon to silver in the nanocomposite and nanocomposite thin film. The lowest carbon to silver molar ratios were attained at the lower end of the pressure range (i.e. 20 Pa). The ratio at 20 Pa was found to be 1.10:1.00. The carbon:silver molar ratio was found to increase with increasing pressures to a maximum of 1.75:1.00 at a pressure of 60 Pa. An increase of pressure beyond 60 Pa to 100 Pa resulted in a similar, yet slightly lower carbon:silver molar ratio of 1.65:1.00. Concurrent with this was the formation of thicker films. At lower pressures (20-60 Pa) a thicker film (up to 1000 nm) was obtained on the substrate, while at the increased pressure of 100 Pa, a much thinner film was achieved.

Vacuum was maintained in the deposition chamber by an evacuation line 124. The deposition chamber was evacuated to a relatively moderate vacuum level of between 20 and 100 Pascals of the hydrocarbon gas n-hexane. The target 120 metal, silver (Ag) was then irradiated with pulsed light laser beam 110 emanating from the laser (not shown). The interaction of the light from the laser and the target causes ejection of atomic and molecular species from the silver target 120, resulted in plume 118. By virtue of the relatively moderate vacuum level, ejected material is slowed by collisions with the background n-hexane gas, which in itself was decomposed by said laser beam when striking the hydrocarbon. This allows the ejected atoms and molecules from the target material to recombine with the decomposition graphite products in the gas phase to effectively produce nanocomposites having a core silver metal and a hydrocarbon and/or carbon and/or graphite shell. The nanocomposites then collect on a substrate 116 held in place inside the deposition chamber 108 by a static fixture 100. The laser irradiation continues for a time sufficient to collect the desired layer of nanocomposite on the substrate 116. In this way, the nanocomposite is a core/shell composite of the silver target nanoparticles, and the carbon from the hydrocarbon gas. The layer of silver/carbon nanocomposite film deposited on the substrate may vary in texture due to the variation of pressure of said hydrocarbon gas, and the time the nanoparticles spend in the laser interaction zone. One skilled in the art will also note that temperature may also affect the texture of said nanocomposite thin film and varying the temperature so as to affect the texture of the nanocomposite thin film is also considered within the scope of this invention. In the preferred embodiment, parameters for the laser, such as pulse energy, repetition rate, pulse duration, wavelength, and beam size, are first set to optimize laser ablation. Adjustments are then made to optimize the generation of carbonization of the hydrocarbon gas so that the carbon to metal ratio in the resulting nanocomposites and nanocomposite films results in desirable nanocomposite thin film textures. In one embodiment the texture of the film, when measured in nm, refers to the average height of protrusions from the surface of the film.

As mentioned above, adjustments may also be made to assure transport of the irradiated, and thus ablated, metal away from the laser interaction zone, such as through the use of confinement and deflection magnetics. This step is important in influencing the overall efficiency and/or amount of carbon deposited on the metal nanoparticles during the laser ablation process, as it can avoid or encourage re-deposition of materials back into the laser interaction zone, thus affecting the core/shell ratio by influencing the graphite deposition on the metal nanoparticles. However, an increase in material found in the laser interaction zone conversely reduces the overall process efficiency of the laser process.

Figure 2:
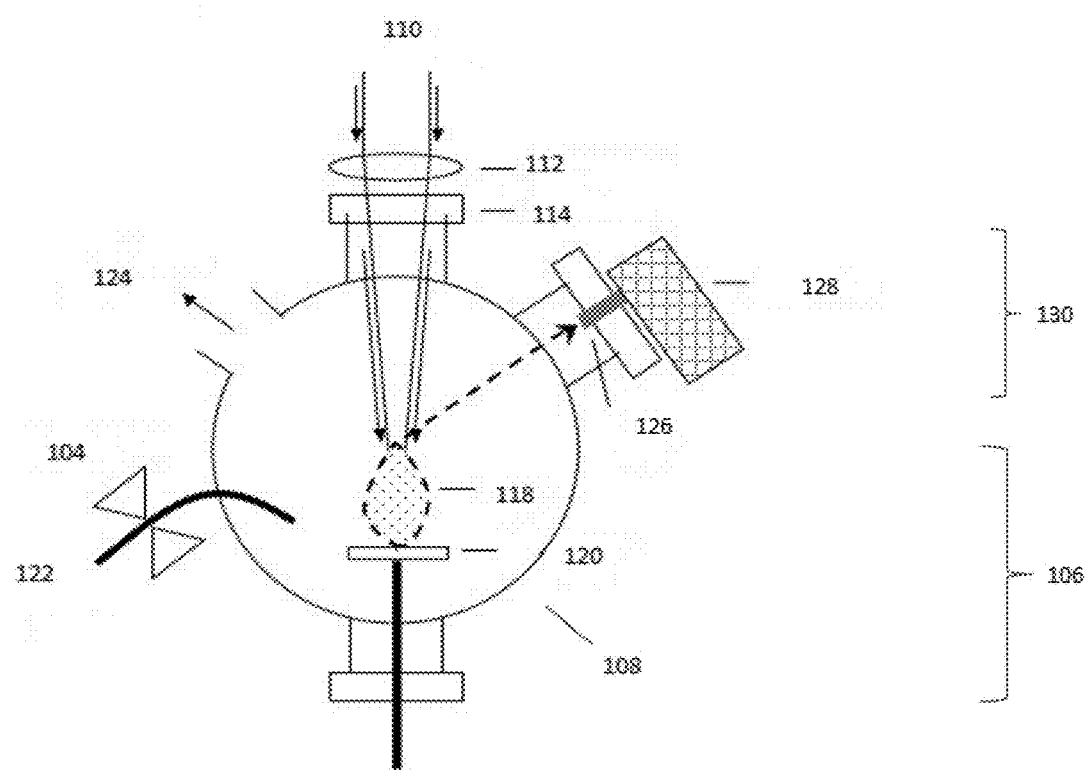
FIG. 2 shows a schematic diagram of the optical emission spectra measurement of a plume produced from silver target.

Referring now to FIG. 2, there is depicted a schematic spectroscopic set up used for the optical emission (OE) investigation of the plume 118. A spectrophotometer system 130, including a photometer 128, and a detector 126, is integrated into the laser ablation setup to record the optical emission (OE) spectra of ablated materials collected from the metal target at various distances from the said target surface. The photometer 128 used to determine the optical properties of said plume may include a UV-vis spectrometer, such as, but not limited to a Shimadzu model. The photometer 128 was used to confirm the release of ionized metal, as well as electrons, from the surface of the target metal in a hydrocarbon atmosphere.

Further to the characterization of the nanomaterials is an analysis by SEM-EDX, TEM-EDX, SAED, FTIR, Raman and UV-Vis absorption analysis, as further discussed below.

The examples below are intended to further illustrate protocols for preparing and characterizing the various embodiments of metal/carbon nanocomposites and nanocomposite thin films described herein, and are not intended to limit the scope of the claims.

Example 1

Ablation of Silver Microparticles in a n-Hexane Vacuum to Form Ag/C Nanocomposites and Texturized Nanocomposite Thin Film: Using the apparatus as shown schematically in FIG. 1, silver nanoparticles were dispersed into an argon stream after a deposition chamber was evacuated to a pressure of 20, 60 or 100 Pascals n-hexane (after distillation on a vacuum line). The pressure of the n-hexane was monitored and controlled by an Edward Barocel pressure sensor (not shown) and a flow line 122 equipped with a PTFE valve 104, respectively. A silver target was irradiated with the output of an ArF 193 nm excimer laser beam as the source of excitation, for a collective irradiation period of 60 seconds. The solid microparticles that were ablated by irradiation resulted in silver nanoparticles. These silver nanoparticles interacted with carbon, in the form of graphite, concurrently released from the decomposition of n-hexane gas, thus forming a silver core and graphite shell (Ag/C) nanocomposite. These nanocomposites were collected downstream from the laser by an amorphous glass substrate 116 positioned at an edge of the spherical glass deposition chamber 108 (diameter=13 cm) opposite the hydrocarbon flow line 122. The as-prepared Ag/C nanocomposite texture was named according to the preparation conditions as illustrated by "Ag/C-x", and wherein "x" (x=20, 60 and 100) was the pressure of n-hexane gas (in units of Pascal) filled inside the deposition chamber 108 before irradiation.

Ag/C nanocomposite thin films were directly deposited on polished NaCl substrates for FT-IR measurements, on quartz substrates during UV-Vis spectra analysis, and on Beryllium substrates for EDX analysis; all under identical experimental conditions as compared to the initial collection of said thin films.

Determining the size distribution of the nanoparticles generated in accordance with the practice of this invention typically requires a large number of individual nanoparticles so that a statistically significant distribution can be obtained. Herein, all measurements were conducted twice and the average value was adopted in the process of collecting the nanoparticles disclosed herein. A scanning electron microscope (SEM) can be used to obtain photomicrographs of nanoparticles. For instance, nanoparticles can be deposited on a quartz substrate and the surface of the quartz substrate can subsequently be scanned to photograph the nanoparticles. In addition, it is well known in the art to employ transmission electron microscopy to obtain images of the nanoparticles. The selected area electron diffraction ("SAED") technique is a crystallographic experimental technique that can be performed inside a transmission electron microscope. As a diffraction technique, it can be used to identify crystal structures and examine crystal defects.

Further techniques include energy-dispersive X-ray spectroscopy ("EDX"), a useful analytical technique for the elemental analysis or chemical characterization of a sample, as it allows for the elemental composition of a sample specimen to be measured via the number and energy of the X-rays emitted form a specimen. Fourier transform infrared spectroscopy is a measurement technique is used to obtain an infrared spectrum of absorption, emission, photoconductivity or Raman scattering of a solid, liquid, or gas. This can be used to identify the decomposition products of n-hexane by ArF excimer laser, as well as the products of the target/hydrocarbon interaction.

Raman spectroscopy is a spectroscopic technique used to observe low-frequency modes in a system. It relies on inelastic scattering of monochromatic light, usually from a laser in the visible, near infrared, or near ultraviolet range. Surface plasmon resonance ("SPR") is the resonant oscillation of conducting electrons at the interface between a negative and positive permittivity material stimulated by incident light. SPR is the basis of many standard tools for measuring adsorption of material onto planar metal surfaces, or onto the surface of metal nanoparticles.

Characterization Methods

The transmission electron microscopy (TEM) images, including selected area electron diffraction (SAED) patterns of as-deposited Ag/C nanocomposites, were recorded on a transmission electron microscope (JSM-6510). Fourier transform infrared spectra (FT-IR) of Ag/C nanocomposites deposited on polished NaCl substrates were recorded at room temperature using a FTIR spectrophotometer (Impact 400, Thermo Nicolet), in order to identify the decomposition products of n-hexane induced by ArF excimer laser.

The decomposition products of carbon that converted from n-hexane under irradiation of ArF excimer laser were further investigated using laser Raman spectrometer ($\lambda$=473 nm, 30% of Power). The deposited solid textures were carefully transferred to a polished tungsten substrate by scratching before the laser Raman spectroscopy measurement. FIG. 2 depicts the acquisition/deposition system 106, spectrometer, 126 and detector 128 of the spectroscopic setup that was used for the optical emission (OE) investigation of the ablation plume. The optical property of as-deposited Ag/C nanocomposite textures on quartz was measured by a UV-Vis spectrometer (Shimadzu). The complete graphite-like structure, —C=C— group and sp3 C—H stretch vibration were observed from Raman and F-IR measurements. The remarkable decrease in optical intensity of the silver plume by increasing the pressure of n-hexane from 60-100 Pa was found, which could be the main reason responsible for the much thinner layer deposited at pressure of 100 Pa. The dependent of SPR position (red-shift amount) on the silver nanoparticles concentration was also noticed and such red shift is deduced to be caused by the mutual polarization of the particles.

SEM-EDX Analysis

Figure 3:
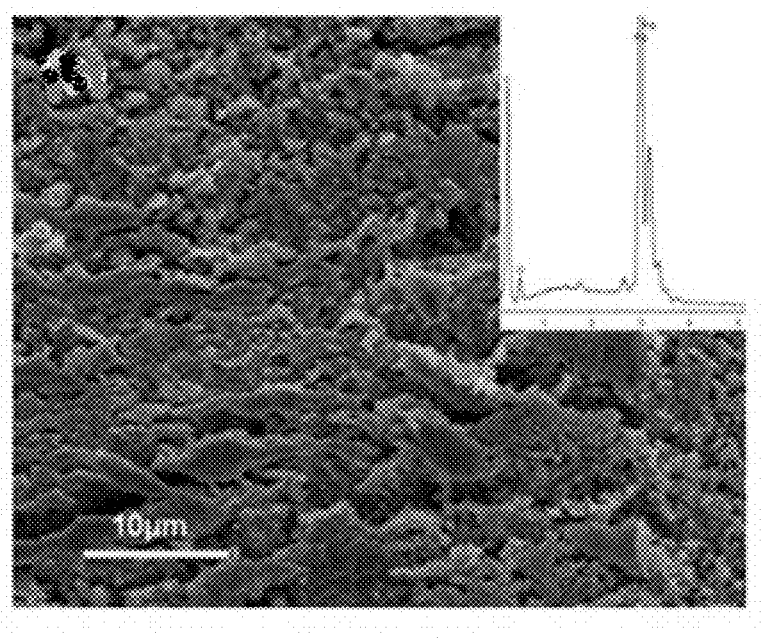
FIG. 3A shows SEM images and corresponding Energy-dispersive X-ray ("EDX") results (inset) of as-deposited Ag/C composite textures prepared in the presence of n-hexane at pressures of 20 Pa.
FIG. 3B shows SEM images and corresponding Energy-dispersive X-ray ("EDX") results (inset) of as-deposited Ag/C composite textures prepared in the presence of n-hexane at 60 Pa.
FIG. 3C shows SEM images and corresponding Energy-dispersive X-ray ("EDX") results (inset) of as-deposited Ag/C composite textures prepared in the presence of n-hexane at 100 Pa.
FIG. 3D shows the molar ratios of carbon to silver at varying pressures of n-hexane.
Figure 3B:
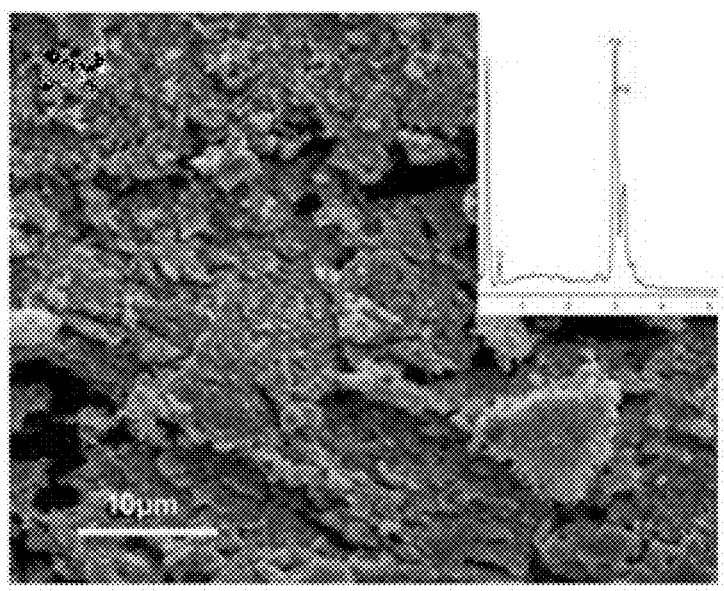
Figure 3:
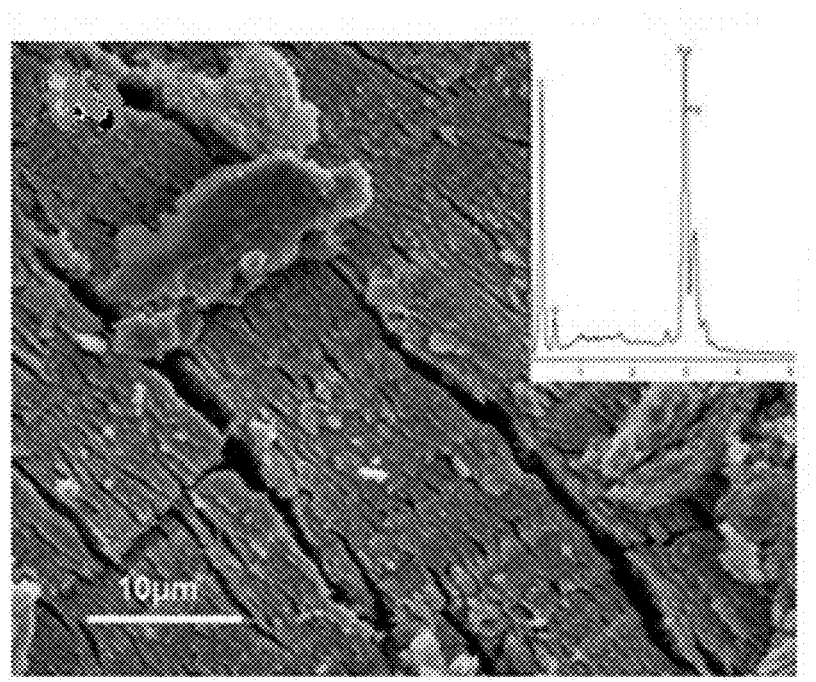
Figure 3:
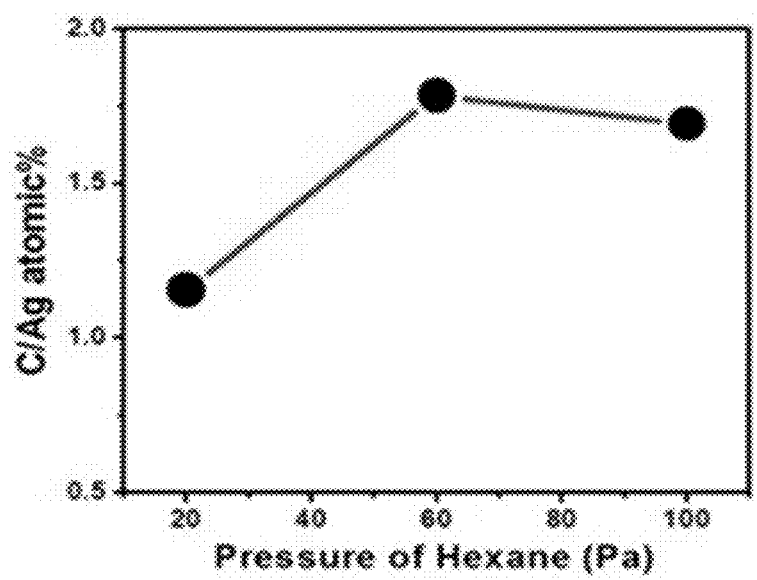

The morphology of as-deposited Ag/C textures was investigated using SEM and the corresponding composition analysis was carried out as well (as depicted in FIG. 3). EDX analysis that was measured on a beryllium substrate suggests the existence of carbon and silver elements. The pressure of n-hexane, the main source of carbon, was the greatest influence on the amount of carbon deposited on the substrate. The product yield of carbon, as well as the molar ratio of carbon to silver, was found to increase with the increase in pressure of n-hexane up to 60 Pa. At that pressure, the molar ratio of carbon to silver reaches 1.75:1. A further increase in pressure of n-hexane above 60 Pa did not yield further increases in product yield of carbon nor improve the ratio of carbon to silver, thus indicating that the saturation of carbon yield was most likely reached by a pressure of n-hexane at 60 Pa. In such situation, it is understood that virtually all the photons from the ArF excimer laser have contributed in the conversion of n-hexane to carbon.

TEM-EDX Analysis

Figure 4C:
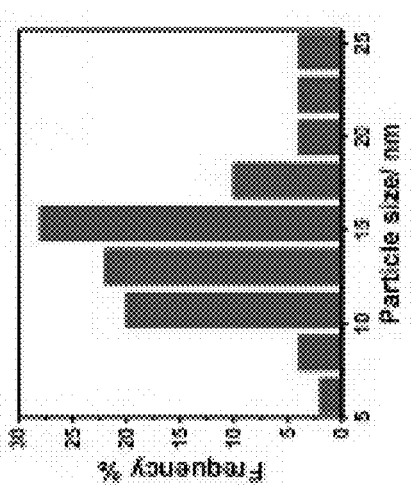
FIG. 4C shows the particle size distributions (sample size=50) obtained from the corresponding selected area electron diffraction ("SAED") patterns from FIG. 4A.
Figure 4B:
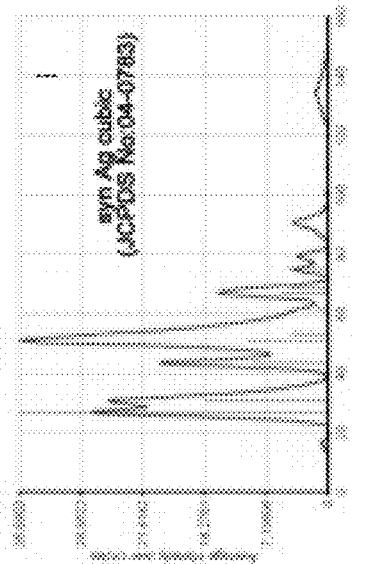
FIG. 4B show the phase results obtained from the corresponding selected area electron diffraction ("SAED") patterns from FIG. 4A.
Figure 4A:
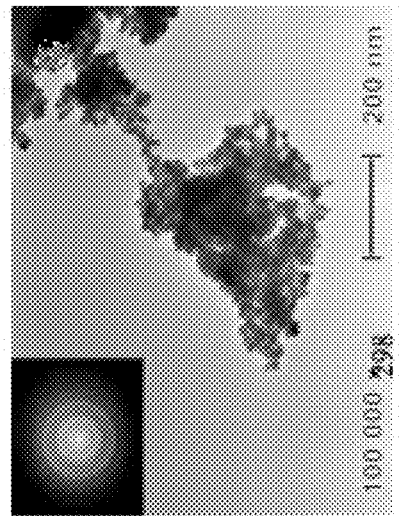
FIG. 4A shows TEM images and the corresponding SAED patterns (inset) of as-deposited Ag/C nanocomposites in the presence of n-hexane at pressures of 20 Pa.

TEM and SAED were carried out to further investigate the morphology and the crystal structures of metallic silver in Ag/C composites deposited in the presence of n-hexane in the 20-100 Pa pressure range. As clear from FIG. 4, spherical nanoparticles with the size of 5-20 nm and relatively narrow size distribution can be clearly observed from the representative TEM images of Ag/C-20 and Ag/C-60. The position and relative intensity of scattering vectors calculated from the SAED pattern, could be well indexed as the existence of cubic silver (JCPDS No. 04-0783), demonstrating the cubic metallic silver were deposited on the substrate after being atomized from the target under excimer laser irradiation.

FT-IR Analysis

Figure 5C:
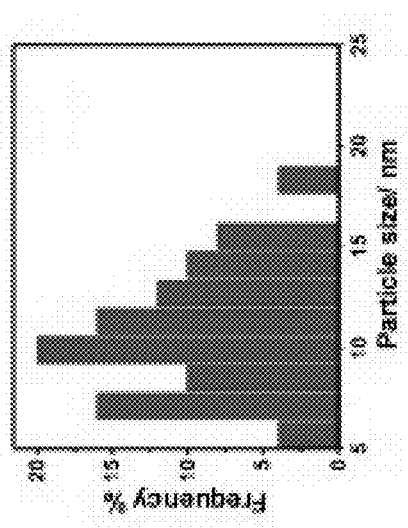
FIG. 5C shows the particle size distributions (sample size=50) obtained from the corresponding selected area electron diffraction ("SAED") patterns from FIG. 5A.
Figure 5B:
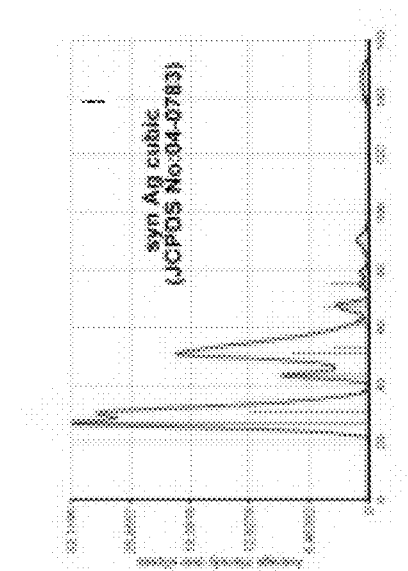
FIG. 5B show the phase results obtained from the corresponding selected area electron diffraction ("SAED") patterns from FIG. 5A.
Figure 5A:
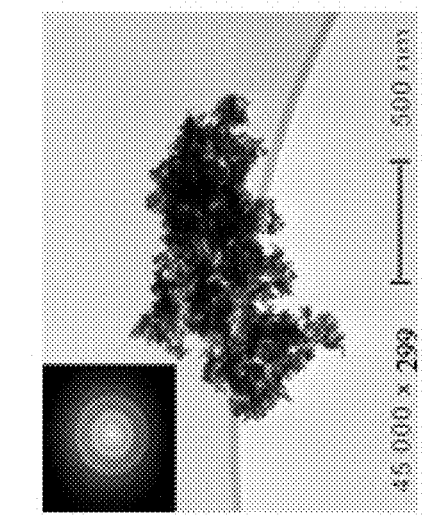
FIG. 5A shows TEM images and the corresponding SAED patterns (inset) of as-deposited Ag/C nanocomposites in the presence of n-hexane at pressures of 60 Pa.

The Ag/C nanocomposite textures were directly deposited on polished NaCl substrates under identical experimental conditions for FT-IR measurement. As depicted in FIG. 5, no peak could be distinguished from the FT-IR spectrum of the Ag/C-100 sample due to the small thickness of as-deposited sample, except the absorption at 2360 cm$^{-1}$ which is attributed to the $CO_2$ asymmetric stretch vibration (not shown). The stretching mode of $C_2$ can be observed at wavenumbers 1562 and 1593 cm$^{-1}$ for the samples Ag/C-20 and Ag/C-60, respectively. Moreover, the sp$^3$ C—H stretch vibration can be observed at wavenumbers centered at 2861/2924/2958 cm$^{-1}$ and 2918 cm$^{-1}$ for the samples Ag/C-20 and Ag/C-60, respectively. The FT-IR results are aligned with the findings of the Raman analysis.

Raman Analysis

Figure 6C:
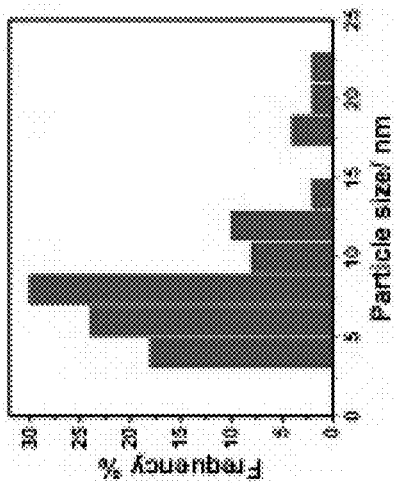
FIG. 6C shows the particle size distributions (sample size=50) obtained from the corresponding selected area electron diffraction ("SAED") patterns from FIG. 6A.
Figure 6B:
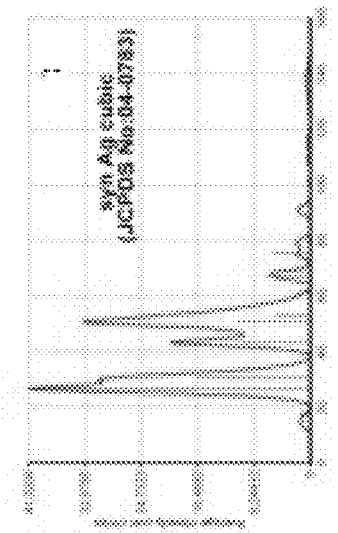
FIG. 6B show the phase results obtained from the corresponding selected area electron diffraction ("SAED") patterns from FIG. 6A.
Figure 6A:
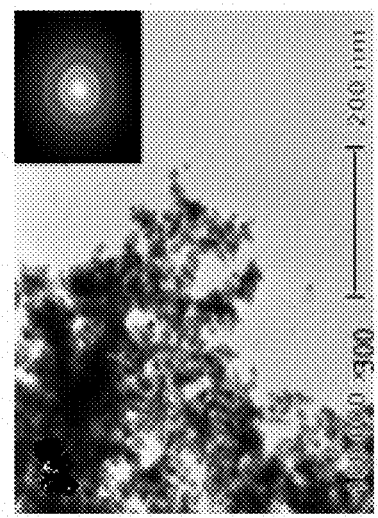
FIG. 6A shows TEM images and the corresponding SAED patterns (inset) of as-deposited Ag/C nanocomposites in the presence of n-hexane at pressures of 100 Pa.

The structure of carbonaceous products converted from n-Hexane by ArF excimer laser was further studied by means of Raman characterization. It should be noticed that only 30% of the incident laser power was utilized during the Raman spectra measurement in order to prevent unnecessary damage (oxidation) of the samples. As depicted in FIG. 6, all of the Ag/C nanocomposite samples display two Raman peaks centered at ~1366 cm$^{-1}$ and 1585 cm$^{-1}$, which correspond to the D band and G band scatterings, respectively. Compared to the broad D band observed, the G band, which is caused by the first-order scattering of the $E_{2g}$ mode observed from sp$^2$ carbon domains, is much sharper and has far higher Raman intensity, demonstrating the existence of carbonaceous products with complete graphite-like structures in the Ag/C nanocomposites.

Optical Emission Spectra During Laser Ablation Process

Figure 7:
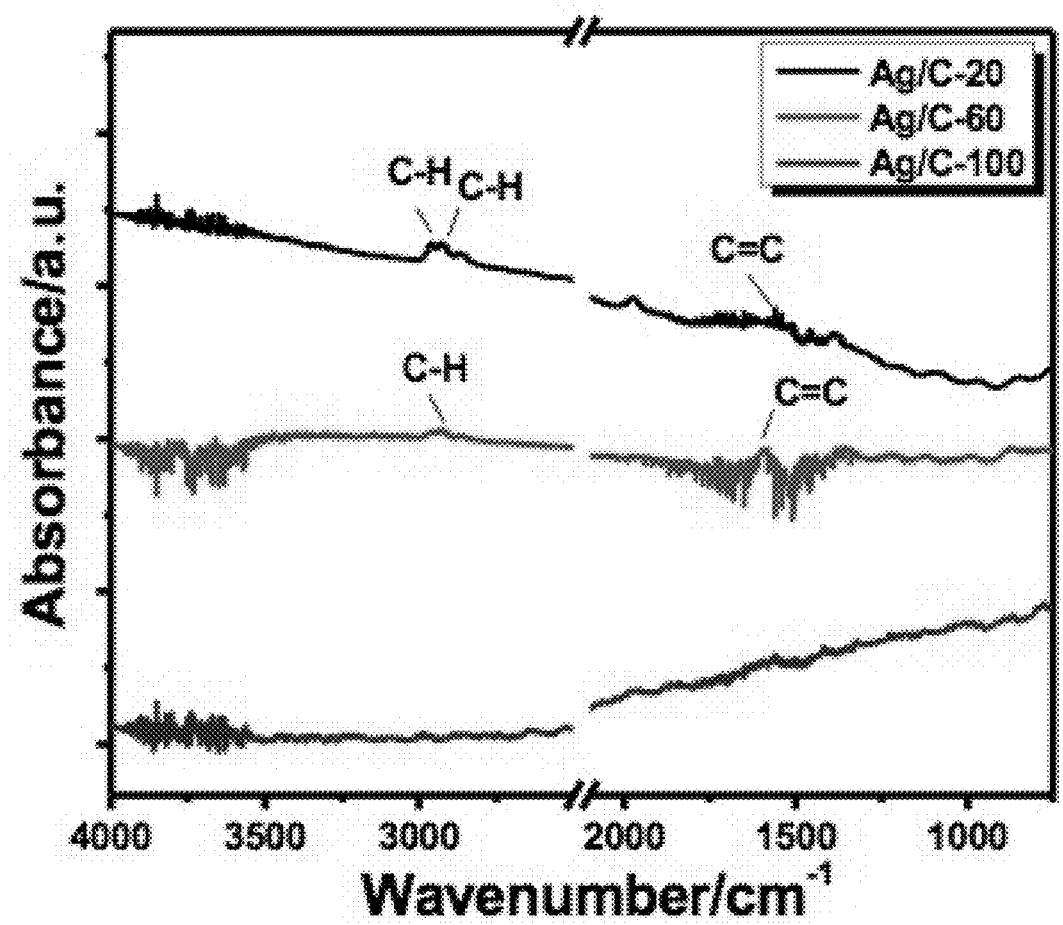
FIG. 7 shows FT-IR spectra of as-deposited Ag/C nanocomposite textures in the presence of n-hexane at different pressures.

FIG. 7 depicts the optical emission spectra collected from the target surface level (d=0 cm) at a distance of 1 cm from the target surface. It can be found that most of the lines exhibited in these spectra could be attributed to the ionized silver. In both cases, the strong lines centered at 519 and 545 nm are identified as the silver transitions of $4d^{10}5p$-$4d^{10}5d$. [A. Striganove, N. Sventiski, Table of Spectral Lines of Neutral and Ionized Atoms, Plenum Press, New York, 1968 Incorporated by reference herein in its entirety.] The strongest line at approximately 385 nm is caused by the second harmonic from the ArF excimer laser. From the optical emission spectra series measured at the surface of target, no apparent changes in the emission intensity in the UV-Vis region were observed in the presence of n-hexane at varying pressures. However, the negative effect of excessive n-hexane on the emission intensity detected at the distance of 10 mm from the target can be visibly discerned in FIG. 7. The OE intensity apparently does not change in the presence of n-hexane at pressures varying from 20 Pa to 60 Pa. Nevertheless, the optical emission intensities at both wavelengths, 518 nm and 546 nm, decrease almost two fold after filling n-hexane in the 60 Pa to 100 Pa pressure range. The ionization energy of silver atoms and the photon energy of the ArF excimer laser ($\lambda$=193 nm) were 7.57623 eV and 6.42 eV respectively. Thus approximately 1.2 photons are needed for the ionization of one silver atom from the target, and concurrently, an electron will be emitted from the target as well. The lower pressure from 20 Pa to 60 Pa of n-hexane may lead to higher emission speed for electrons. This facilitates the recombination of electrons and ions or atoms; therefore, a much thicker texture is obtained. In contrast, a further increase in the pressure of n-hexane, for example to 100 Pa, inhibits the emission speed of electrons, giving rise to thinner films.

UV-Vis Absorption Analysis

Figure 8:
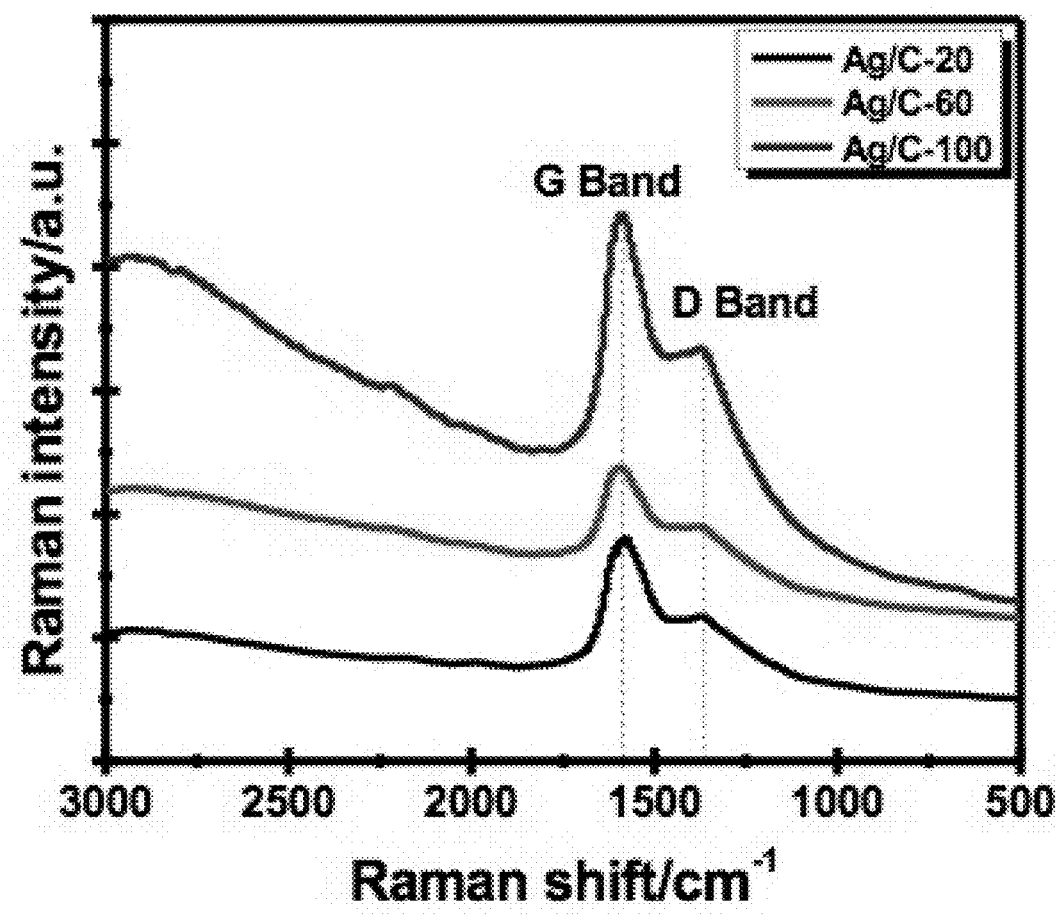
FIG. 8 shows Raman spectra of Ag/C nanocomposites deposited in the presence of n-hexane at different pressures.
Figure 9:
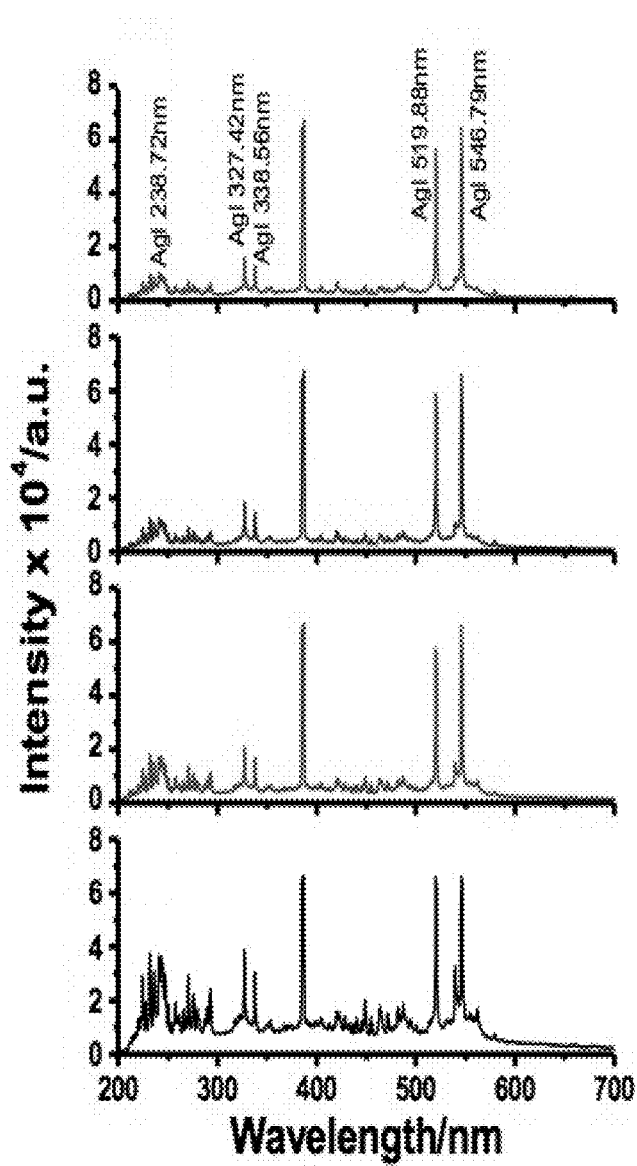
FIGS. 9A, 9B, 9C and 9D shows Optical emission spectra of ionized silver plasma generated by the ArF excimer laser at the distance of 0 mm away from the target surface in the presence of n-hexane at different pressures of 0 Pa (A), 20 Pa (B), 60 Pa (C) and 100 Pa (D), respectively.
Figure 10:
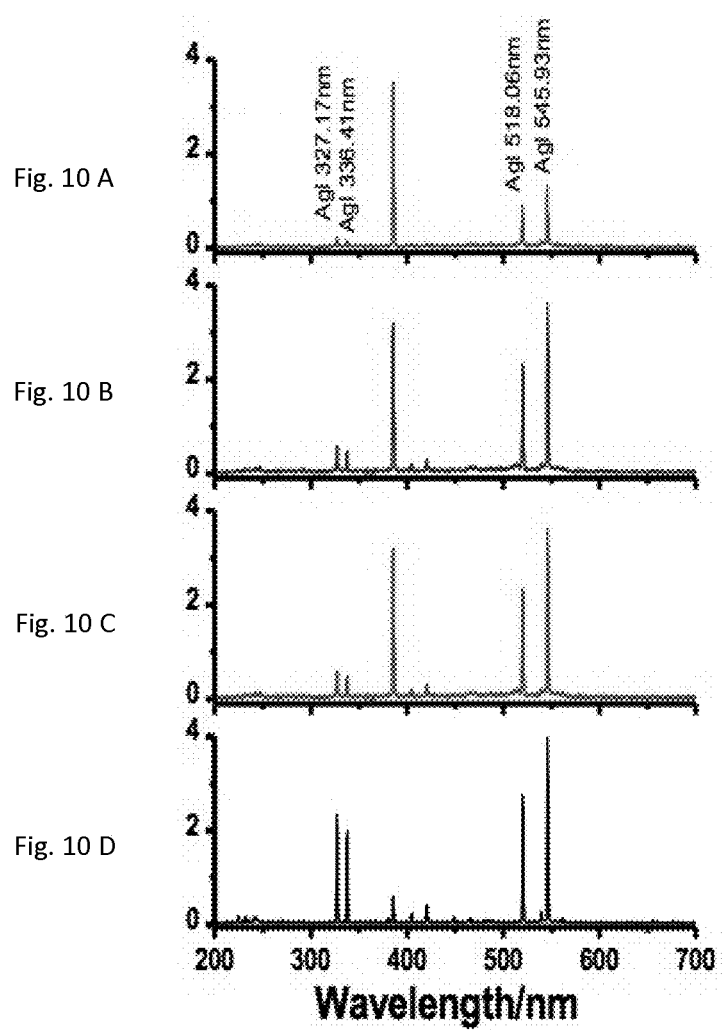
FIGS. 10A, 10B, 10C and 10D shows Optical emission spectra of ionized silver plasma generated by the ArF excimer laser at the distance of 10 mm away from the target surface in the presence of n-hexane at different pressures of 0 Pa (A), 20 Pa (B), 60 Pa (C) and 100 Pa (D), respectively.
Figure 11:
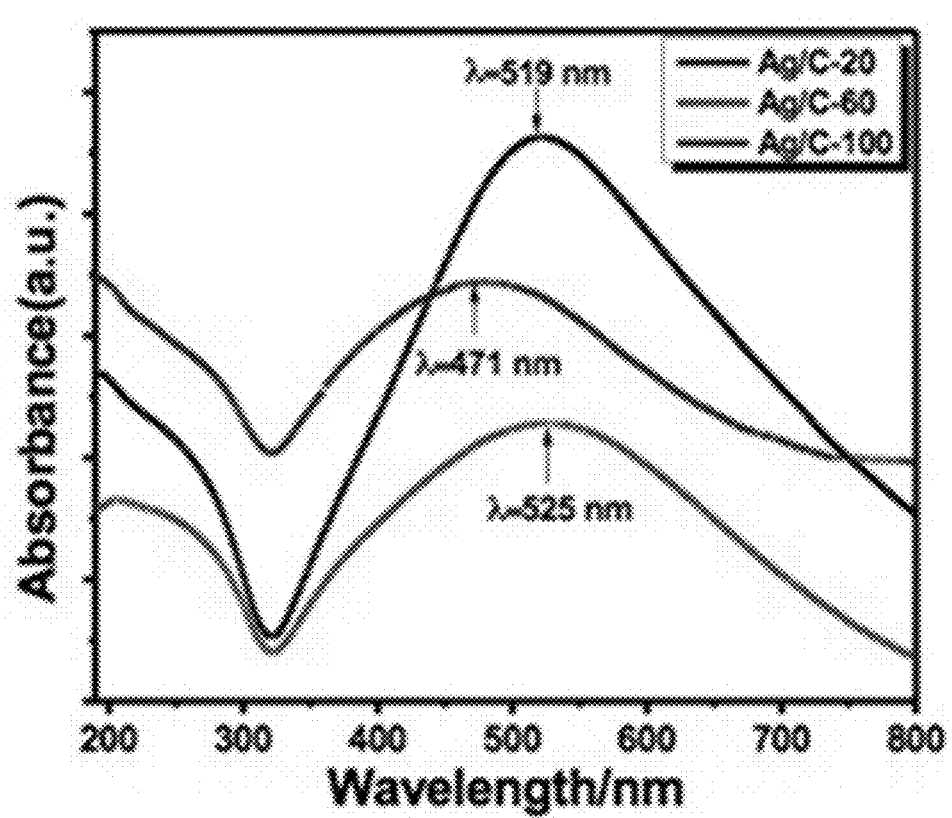
FIG. 11 shows UV-Vis spectra of Ag/C composite textures on quartz substrates deposited in the presence of n-hexane at pressures of 20 Pa, 60 Pa and 100 Pa, respectively.

Silver particles can be identified by UV-Vis absorption measurements, as silver particles exhibit an intense absorption band caused by the surface plasmonic excitation. As depicted in FIG. 8, the absorption bands in the visible region suggest that silver nanoparticles are produced. The absorption peak of the Ag/C composites deposited in the presence of n-hexane at 20 Pa is centered at 519 nm. The small red-shift to 471 nm (~50 nm of shift) can be found when increasing the pressure of n-hexane to 60 Pa (increasing the carbon/silver molar ratios from 1.1 to 1.75. Furthermore, the Ag/C-100 sample which has a similar molar ratio of carbon/silver compared with sample of Ag/C-60, exhibits a similar surface Plasmon resonance (SPR) position centered at approximately 525 nm. These results clearly suggest that the SPR position is strongly dependent on the concentration of metal (silver) nanoparticles in the composites, and is most likely caused by the mutual polarizations of the particles. Conclusively, the method of producing metal/carbon nanocomposites and nanocomposite thin films with variations in texture was carried out within a relatively short time frame of 60 seconds, and produced the largest molar ratio of carbon graphite to silver nanoparticles at a n-hexane pressure of 60 Pascals.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method of preparing a core/shell nanocomposite thin film comprising:
    concurrently irradiating a silver metal target and n-hexane gas, present within a deposition chamber, with an excimer laser beam;
    wherein the irradiating forms carbon in the form of graphite from the n-hexane gas, and silver nanoparticles of said silver metal target which are spherical or cubic in form, thereby forming core/shell nanocomposite particles having a silver nanoparticle core covered by a graphite shell;
    wherein the core/shell nanocomposite particles form a nanocomposite thin film on a substrate within the deposition chamber;
    wherein the pressure of the n-hexane gas in the deposition chamber during the irradiating is within a range of 20-100 Pascal.

2. The method of claim 1, which forms the nanocomposite thin film within 30-90 seconds.

3. The method of claim 1, further comprising varying the pressure of the n-hexane gas to vary a mass ratio of carbon to metal in the core/shell nanocomposite particles.

4. The method of claim 1, wherein the irradiating forms the core/shell nanocomposite particles having an average particle size of 5-20 nm in diameter.

5. The method of claim 1, wherein the excimer laser beam is generated by an excimer laser selected from the group consisting of ArF and KrF excimer lasers having a beam wavelength of 193 nm-300 nm.

6. The method of claim 5, wherein the excimer laser is an ArF excimer laser with a wavelength of 193 nm.

7. The method of claim 1, wherein the core/shell nanocomposite particles have absorption peaks in a range from 417 nm-525 nm.

8. The method of claim 1, wherein the nanocomposite thin film forms a coating for a biomedical device.

9. The method of claim 8, wherein the biomedical device is a stent.

10. The method of claim 1, wherein the core/shell nanocomposite thin film forms a coating for a solar light harvesting device or sensor.

11. The method of claim 1, wherein the core/shell nanocomposite thin film is present on a surface of a water purification apparatus.

12. The method of claim 11, wherein the water purification apparatus has a plasmonic photocatalysis surface.

13. The method of claim 11, wherein the water purification apparatus includes a nanocomposite thin film surface-enhanced Raman spectroscopy sensor.

14. A method for forming a silver/carbon nanocomposite from a solid silver metal target during an excimer laser ablation process comprising:
   providing a deposition chamber;
   placing the solid silver metal target and a substrate within said deposition chamber;
   establishing a vacuum level within said deposition chamber so as to achieve a reduced atmospheric pressure;
   introducing n-hexane into said deposition chamber wherein said n-hexane is in a vapor phase due to the reduced atmospheric pressure and furthermore wherein said n-hexane vapor fills said deposition chamber and is in contact with said solid silver metal target;
   focusing an excimer laser beam onto the solid silver metal target in contact with the n-hexane vapor at a power density high enough to release cubic or spherical uniformly-sized silver nanoparticles from the solid silver metal substrate;
   concurrently irradiating said n-hexane vapor with the excimer laser beam at a power density high enough to cause decomposition of the n-hexane vapor;
   said irradiation causing a carbonization, in the form of graphite, of said silver nanoparticles to form core/shell nanocomposite particles having a silver nanoparticle core covered by a graphite shell;
   collecting said core/shell nanocomposite particles on said substrate to form a core/shell nanocomposite thin film;
   wherein varying the chamber vacuum level results in fluctuation of the n-hexane vapor pressure in the range of 20-100 Pascal, affecting the ratio of carbon to silver in the silver/carbon nanocomposite, and resulting in deposition texture variations of the core/shell nanocomposite thin film.

* * * * *